United States Patent
Ritter et al.

(10) Patent No.: US 10,024,793 B2
(45) Date of Patent: Jul. 17, 2018

(54) METHOD FOR THREE-DIMENSIONAL HIGH RESOLUTION LOCALIZATION MICROSCOPY

(71) Applicant: Carl Zeiss Microscopy GmbH, Jena (DE)

(72) Inventors: Jörg Ritter, Jena (DE); Jörg Siebenmorgen, Jena (DE); Thomas Kalkbrenner, Jena (DE)

(73) Assignee: Carl Zeiss Microscopy GmbH, Jena (DE)

( * ) Notice: Subject to any disclaimer, the term of this patent is extended or adjusted under 35 U.S.C. 154(b) by 695 days.

(21) Appl. No.: 14/276,167

(22) Filed: May 13, 2014

(65) Prior Publication Data

US 2014/0340483 A1    Nov. 20, 2014

(30) Foreign Application Priority Data

May 14, 2013  (DE) .................. 10 2013 208 926

(51) Int. Cl.
*H04N 13/02* (2006.01)
*G01N 21/64* (2006.01)
(Continued)

(52) U.S. Cl.
CPC ..... *G01N 21/6458* (2013.01); *G02B 21/0076* (2013.01); *G02B 21/16* (2013.01);
(Continued)

(58) Field of Classification Search
CPC ........... G01N 21/6458; G02B 21/0076; G02B 21/16; G02B 21/361; G02B 21/365; G02B 21/367; G02B 27/58; H04N 13/02
(Continued)

(56) References Cited

U.S. PATENT DOCUMENTS

| 7,675,045 B1 | 3/2010 | Werner et al. |
| 8,362,448 B2 | 1/2013 | Wolleschensky et al. |

(Continued)

FOREIGN PATENT DOCUMENTS

| DE | 10 2008 009 216 | 8/2009 |
| DE | 10 2009 043 744 | 3/2011 |

(Continued)

OTHER PUBLICATIONS

T. Vettenburg et al., "Increasing the resolution of light sheet microscopy in the presence of aberrations", Proceedingts of SPIE, Bd. 8589, Feb. 22, 2013, ISSN:0277-786X, DOI:10.117/12.2003828.*

(Continued)

*Primary Examiner* — Jessica M Prince
(74) *Attorney, Agent, or Firm* — Haug Partners LLP

(57) ABSTRACT

A three-dimensional high-resolution localization microscopy method including illuminating a sample by excitation radiation to excite fluorescence markers in the sample to luminesce, and imaging the sample in an image frame via imaging optics along an imaging direction, wherein the image frame contains images of the luminescing fluorescence markers, and the imaging optics have a plane of focus and an optical resolution. The excitation step and imaging steps are repeated multiple times to generate a plurality of image frames, wherein the excitation steps are performed to isolate the images of the luminescing fluorescence markers in each image frame for at least some of the luminescing fluorescence markers. The location of the corresponding fluorescence marker is determined in each instance in the generated plurality of image frames from the isolated images of the luminescing fluorescence markers, and a highly resolved total image is generated from the locations determined in this way.

8 Claims, 6 Drawing Sheets

(51) Int. Cl.
*G02B 21/16* (2006.01)
*G02B 21/36* (2006.01)
*G02B 21/00* (2006.01)
*G02B 27/58* (2006.01)

(52) U.S. Cl.
CPC ......... *G02B 21/361* (2013.01); *G02B 21/365* (2013.01); *G02B 21/367* (2013.01); *G02B 27/58* (2013.01); *H04N 13/02* (2013.01)

(58) Field of Classification Search
USPC ......................................................... 348/46
See application file for complete search history.

(56) References Cited

U.S. PATENT DOCUMENTS

| | | | |
|---|---|---|---|
| 2009/0134342 | A1 | 5/2009 | Hell et al. |
| 2009/0242798 | A1 | 10/2009 | Bewersdorf et al. |
| 2010/0160613 | A1 | 6/2010 | Seyfried et al. |
| 2010/0265318 | A1 | 10/2010 | Bewersdorf et al. |
| 2011/0036996 | A1* | 2/2011 | Wolleschensky .. G01N 21/6458 250/459.1 |
| 2011/0043619 | A1* | 2/2011 | Wolleschensky .. G01N 21/6428 348/79 |
| 2012/0200693 | A1* | 8/2012 | Lippert ................ G02B 21/002 348/79 |
| 2012/0224034 | A1* | 9/2012 | Kalkbrenner ...... G01N 21/6458 348/49 |
| 2013/0010098 | A1 | 1/2013 | Kalkbrenner et al. |
| 2013/0302905 | A1 | 11/2013 | Kalkbrenner et al. |
| 2014/0346328 | A1 | 11/2014 | Niu et al. |
| 2015/0029325 | A1* | 1/2015 | Dholakia ........... G01N 21/6458 348/79 |

FOREIGN PATENT DOCUMENTS

| | | |
|---|---|---|
| DE | 10 2009 060793 | 7/2011 |
| DE | 10 2010 044 013 | 5/2012 |
| JP | 2011-508214 | 3/2011 |
| JP | 2011-511966 | 4/2011 |
| JP | 2013-057938 | 3/2013 |
| JP | 2013-515249 | 5/2013 |
| JP | 2014-501915 | 1/2014 |
| JP | 2014-521093 | 8/2014 |

OTHER PUBLICATIONS

European Search Report (EP 14 16 7996) dated Sep. 5, 2014.
T. Vettenburg et al: "Increasing the resolution of light sheet microscopy in the presence of aberrations", Proceeding of SPIE, Bd. 8589, Feb. 22, 2013, ISSN: 0277-786X, DOI: 10.1117/12.2003828.
German Search Report (DE 10 2013 208 926.0) dated Mar. 20, 2014.
Notification of Reason for Rejection for JP Application No. 2014-094231 dated Mar. 6, 2018

* cited by examiner

METHOD FOR THREE-DIMENSIONAL HIGH RESOLUTION LOCALIZATION MICROSCOPY

The present application claims priority from German Patent Application No. DE 10 2013 208 926.0 filed on May 14, 2013, the disclosure of which is incorporated herein by reference in its entirety.

FIELD OF THE INVENTION

The invention is directed to a method for three-dimensional high-resolution localization microscopy in which a sample is illuminated by excitation radiation in an excitation step in order to excite fluorescence markers in the sample to luminesce, the sample is imaged in an image frame in an imaging step by means of imaging optics along an imaging direction, wherein the image frame contains images of the luminescing fluorescence markers, and the imaging optics have a plane of focus and an optical resolution, the excitation step and imaging step are repeated multiple times so that a plurality of image frames are generated, wherein the excitation steps are carried out such that the images of the luminescing fluorescence markers are isolated in each image frame for at least some of the luminescing fluorescence markers, a location of the corresponding fluorescence marker is determined in each instance in the generated plurality of image frames from the isolated images of the luminescing fluorescence markers, which location has an accuracy exceeding the optical resolution, and a highly resolved total image is generated from the locations determined in this way.

It is noted that citation or identification of any document in this application is not an admission that such document is available as prior art to the present invention.

Various methods have been developed in the art for overcoming diffraction limits in microscopy. A method abbreviated as PALM (photoactivated localization microscopy) is known from WO 2006/0127692 or DE 102006021317 A1. For imaging a sample, this method uses a labeling substance which can be activated by optical radiation. The labeling substance can emit determined fluorescence radiation only in the activated state. Molecules of the labeling substance that are not activated do not emit fluorescence radiation, or at least no observable fluorescence radiation, having the defined characteristics even after being irradiated by excitation radiation. Therefore, the activation radiation is referred to in general as switching signal. In the PALM method, the switching signal is applied in such a manner that at least some of the activated labeling molecules are at a distance from adjacent activated labeling molecules such that, measured at the optical resolution of the microscope, they are separated or can be separated subsequently by image processing methods. Fluorescence markers are referred to as isolated, and this section is also referred to as isolation step. In this respect, it is sufficient to isolate a partial amount of the total amount of fluorescence markers. The sample is imaged in such a way that there is obtained an image frame of the sample in which at least some fluorescence markers luminesce in isolation. The center of the recorded radiation distribution which, of course, is not point-shaped due to limiting resolution is then determined for each fluorescence marker. In this way, the position of the fluorescence marker is localized computationally with higher accuracy than would actually be permitted by the optical resolution. This step is referred to as the localization step.

The steps of isolation and localization are carried out repeatedly so that a plurality of image frames is obtained. Ideally, every fluorescence marker is isolated once in at least one image frame. The location information determined from the image frames makes it possible to generate a total image which contains the location information of the individual fluorescence markers with an accuracy in each instance that exceeds the optical resolution. An image of this kind having an accuracy enhanced beyond the optical resolution is referred to as high resolution.

The PALM principle uses statistical effects to isolate the fluorescence markers. With a fluorescence marker that can be activated by the switching signal at a given intensity for fluorescence radiation, it can be ensured by adjusting the intensity of the switching signal that the probability of activating fluorescence markers present in a given surface region of the sample is so slight that there are sufficient sub-regions in the imaged sample in which at least some isolated fluorescence markers can be excited within the optical resolution for emitting fluorescence radiation. The excitation of the sample activated in this way then leads to fluorescence markers luminescing in isolation.

The PALM principle was further refined with respect to activation, i.e., the application of the switching signal. For example, in molecules having a long-lived nonfluorescing state and a short-lived fluorescing state, there is no need at all for separate activation with activation radiation diverging spectrally from the excitation radiation. On the contrary, the sample is first illuminated by excitation radiation of high intensity such that the vast majority of molecules is in a long-lived state of non-fluorescence (e.g., a triplet state). The remaining molecules that are then still fluorescing are then at least partially isolated.

In the interim, the PALM principle has also adopted other abbreviations in the technical literature, e.g., STORM, etc. In the present specification, the abbreviation PALM is used to denote any microscopy techniques which achieve a high resolution by first isolating and then localizing fluorescence markers. The PALM method has the advantage that high spatial resolution is not required for excitation. Simple widefield illumination is possible.

The PALM principle achieves the high resolution in two dimensions or laterally, i.e., transverse to the imaging direction, because localization can only be carried out for fluorescence markers which are isolated in projection on a plane perpendicular to the imaging direction. Fluorescence markers located behind one another along the imaging direction, i.e., in depth direction, cannot be distinguished by the PALM method per se. For this reason, the first experimental implementations of the PALM method used a TIRF illumination to ensure that fluorescence markers are excited only from a sharply defined depth region that is appreciably smaller than the depth of field of the imaging optics employed.

In the meantime, the prior art has yielded further methods and approaches which achieve a three-dimensional localization microscopy in which fluorescence markers are also isolated and localized in the third spatial direction, i.e., with respect to imaging in the depth direction.

An imaging beam path in which is located a weak cylindrical lens leading to a deliberate astigmatic distortion in the image is described for the PALM principle in the publication by B. Huang et al., Science 319, page 810, 2008. Accordingly, the image of every fluorescence marker on the camera is elliptically distorted whenever the fluorescence marker is located above or below the plane of focus which presents a point of symmetry of the point spread function of the image of the sample. Information about the depth position of the luminescing fluorescence marker can be obtained from the orientation and magnitude of the distortion. A drawback of this method consists in that in the case of a molecular dipole the local surroundings and orientation thereof can lead to a distortion of the image of the luminescing fluorescence markets which, however, has nothing to do with the depth position. Luminescing fluorescence markers of this kind then acquire a false depth value depending on their spatial position.

The publication by Shtengel et al. PNAS 106, page 3125, 2009, takes another approach. In this case, photons which are emitted by the luminescing fluorescence markers are made to interfere with each other. For this purpose, two objectives mounted in 4π configuration are used to observe the luminescing fluorescence markers simultaneously. By means of a special three-way beamsplitter, the radiation from the partial beam paths obtained in this way are interfered with each other. Each of the images obtained is detected by a camera and the intensity ratios of the images give information about the depth position.

In the publications by Toprak et al., Nanolet 7, pages 3285-3290, 2009, and Juette et al., Nature Methods 5, page 527, 2008, a 1:1 beamsplitter splitting the image of the sample into two partial images which are detected independently is installed in the imaging beam path. In addition, an optical path length difference is introduced in one of the partial beam paths downstream of the beamsplitter such that the two partial beam paths image two object planes which are spaced apart by approximately one half of, or all of, the minimum optical resolution in the depth direction. The depth position of a fluorescence marker located between these two object planes is obtained by analyzing the two partial images of this fluorescence marker (e.g., with respect to the width of the point spread function). The method requires two highly resolved partial images and a subpixel-exact superposition of these two partial images. A refinement of this approach which drastically reduces the alignment time is known from DE 102009060490 A1.

A principle of depth resolution in localization microscopy tracks the deliberate distortion of the point spread function (also abbreviated hereinafter as PSF) of the image. This kind of approach is described, for example, in WO 2012/039636 which modifies during imaging of the sample such that an image distortion occurs which is dependent on the depth position. For example, the point spread function, which is ideally elliptical, is modified to a kind of helix structure such that, instead of a diffraction disk, two neighboring lobes are used for imaging a luminescing spot, the relative position of these two lobes being dependent upon the depth position of the imaged luminescing spot.

A further principle for acquiring depth information in three-dimensional localization microscopy is found in DE 102010044031 A1. For excitation radiation and/or switching radiation, it utilizes so-called light sheet illumination, which is described, for example, in the publication by P. Keller and E. Stelzer, "Quantitative In Vivo Imaging of Entire Embryos with Digital Scanned Laser Light Sheet Fluorescence Microscopy", Current Opinion in Neurobiology, 2009, vol. 19, pages 1-9. The sample is illuminated successively by two light sheets which are axially offset relative to one another but which overlap. Molecules which radiate fluorescence radiation in both light sheet positions must necessarily be located in the overlapping region of the two light sheet positions. Therefore, suitable filtering is carried out. In this way, the depth selection can be increased appreciably beyond the thickness of the light sheet. The thickness of the overlapping area is crucial for filtering. This approach has the drawback that twice the quantity of image frames must be taken for localization, that is, the quantity of image frames that would be required for conventional PALM imaging for each light sheet position. Also, the precise adjustment of the offset of the light sheets and particularly the reproducibility of the displacement is essential for the thickness of the overlapping area and, therefore, for the depth resolution. Finally, in general, no meaningful resolution can occur within the filtered-out overlapping area. Therefore, the overlapping area defines a kind of measurement uncertainty with regard to the depth information. Fluorescence markers located outside of the overlapping area cannot be specified in terms of their depth position so that ultimately a scan of the sample is required in order to capture an area larger than the overlapping area.

In addition, unwanted irradiation of the fluorescence markers can be disadvantageous in PAL microscopy because often the fluorescence markers can only undergo a very limited quantity of activation cycles and/or excitation cycles. In this sense, any irradiation that is not utilized for high-resolution imaging is unwanted. The principle of overlapping light sheets is also capable of improvement in this respect because in this case fluorescence markers are irradiated whose depth position is not acquired for the reason that they lie outside of the overlapping area.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

It is further noted that the invention does not intend to encompass within the scope of the invention any previously disclosed product, process of making the product or method of using the product, which meets the written description and enablement requirements of the USPTO (35 U.S.C. 112, first paragraph), such that applicant(s) reserve the right to disclaim, and hereby disclose a disclaimer of, any previously described product, method of making the product, or process of using the product.

SUMMARY OF THE INVENTION

It is the object of the invention to further develop the microscopy method from DE 102010044013 A1 in such a way that depth information can be determined within a larger depth region without being limited depending on whether or not a fluorescent molecule is located within a given depth region. The invention has the further object of providing a depth-resolving microscopy method which prevents unwanted illumination of fluorescence markers as far as possible.

The above-stated object is met according to the invention by a method of the type mentioned above which is characterized in that the excitation radiation is passed into the sample as a first light sheet having along the imaging direction an intensity distribution that is asymmetric to the plane of focus, the isolated images of the luminescing fluorescence markers are analyzed with respect to the contour shape thereof in the image frames, and information about the distance of the corresponding fluorescence marker from the plane of focus is derived from the contour shape.

By "fluorescence marker" is meant in the present specification a fluorescence emitter that is suitable for localization microscopy, i.e., can be used to cause individual fluorescence markers to luminesce in isolation with respect to the optical resolution. The term "fluorescence marker" also covers cases where structures in a sample are labeled with corresponding substances as well as cases where the sample itself already has the suitable fluorescence characteristics.

The invention uses light sheet microscopy to generate a point spread function which depends on the depth direction. Accordingly, it employs the light sheet used in DE 102010044013 A1 to configure imaging such that the point spread function depends on the depth direction. This shall also be referred to as the axial dependency of the point spread function (PSF). An axial dependency of the point spread function is generated by virtue of the fact that the light sheet is asymmetrical to the plane of focus with respect to its intensity distribution. It is appreciated by the inventors that the point spread function is only axially symmetrical in light sheet microscopy when the light sheet is symmetric to the plane of focus. On the other hand, if the light sheet is asymmetrical axial to the plane of focus, e.g., shifted, there occurs an interruption of symmetry. Since the point spread function of a light sheet microscope is always a combination of excitation and detection, an asymmetry of the light sheet also deforms the point spread function asymmetrically with respect to the plane of focus. In this case, the centroid of the intensity distribution of the point spread function shifts precisely in the direction in which the centroid of the light sheet is also asymmetrical with respect to the plane of focus, for example, in which a light sheet is offset with respect to the plane of focus. Owing to this asymmetry, the isolated images of the luminescing fluorescence markers are analyzed with respect to their contour shape, and the axial position, i.e., the depth position of the fluorescence marker, is unequivocally determined therefrom. To this end, the outer shape, i.e., the contour shape of the isolated image of every luminescing fluorescence marker is analyzed. In this analysis, the width of the intensity distribution of the isolated images is preferably evaluated.

The greater the asymmetry of the intensity distribution of the light sheet with respect to the plane of focus, the simpler it is to axially localize the fluorescence marker, since the asymmetry of the point spread function increases with the asymmetry of the intensity distribution of the light sheet relative to the plane of focus.

In principle, the same algorithms as those otherwise used in the prior art for evaluating asymmetrical point spread functions can be used for the image analysis, for example, the algorithms known from the above-cited publication by Juette et al. The starting point for algorithms of this kind is usually the point spread function of the imaging optics which has been determined beforehand. It can be determined theoretically or empirically on the basis of luminescing points of known dimensions as is also known from WO 2012/039636 cited above.

For the method according to the invention, it is advantageous to image the sample on a detector lying in a plane conjugate to the plane of focus in the imaging step. The asymmetry of the point spread function is then maximal for a given configuration of the light sheet.

The asymmetrical intensity distribution of the light sheet with respect to the plane of focus can then be achieved in that a symmetrical light sheet is generated, which is particularly simple in technical terms, and is arranged such that the maximum of the intensity distribution lies outside the plane of focus. Of course, this can also be carried out for an intensity distribution that is not symmetrical.

Another option for interruption of symmetry consists in illuminating not only with the first light sheet but also with a second light sheet and using two detectors on which the sample is imaged in the imaging step, one of which detectors is located in front of a plane which is conjugate to the plane of focus and the other behind a plane which is conjugate to the plane of focus.

The first light sheet and second light sheet can then even be offset relative to the plane of focus symmetrically with respect to one another. Considered in themselves, they are asymmetrical to the plane of focus. The point spread function is then symmetrical in this case for the total analysis, but an unequivocal axial localization is again possible through the association of the cameras with the planes above and below the plane conjugate to the plane of focus. A larger axial area can be observed simultaneously.

For these two embodiments, a particularly high photon yield is achieved when the imaging optics are configured in such a way that they have two opposing detection objectives. While this does require two complete detection beam paths, the photons detected through the objective need not be distributed to two detectors through a beamsplitter so that only one half of the photons would be used for generating images per camera.

An asymmetric point spread function can also be generated with a plurality of light sheets in that one light sheet lies closer to the plane of focus than the other without the light sheets overlapping. The term "overlapping" refers to a given drop in intensity to define the boundary of the light sheet. A usual boundary is a drop in intensity to 1/e, for example. Other definitions are equally possible. For example, the second light sheet lies in the plane of focus and the first light sheet lies in a non-overlapping manner above or below the plane of focus. An asymmetrical point spread function which is further extended in depth direction is obtained in this way so that the axial localization takes place over a larger depth area. Of course, even more light sheets can also be used for this variant. The difference as opposed to the above-mentioned principle with overlapping light sheets is that by analyzing the contour shape the detection is not limited to the overlapping area and, above all, no filtering is carried out on the overlapping area.

A further difference as opposed to the concept in DE 102010044013 A1 consists in that, with respect to the detection duration for an individual image frame, all of the light sheets used in the invention are radiated simultaneously and not alternately as would be required for filtering. The same effect can also be achieved by illuminating with only one light sheet and using imaging optics having two opposing detection objectives and subsequent detection beam paths, i.e., detectors. It is important here that the planes of focus of the two detection objectives do not coincide.

Aside from geometric possibilities for generating an asymmetric PSF, the wavelength can also be used for this purpose in an embodiment form. When the sample is illuminated by the first light sheet and by a second light sheet and the radiation is detected by the imaging optics in two spectrally separated channels, each color channel is assigned to one of the light sheets, which allows unequivocal axial resolution. However, this requires that the fluorescence markers comprise two spectrally distinct species or two spectrally distinct excitation spectra and emission spectra.

When a plurality of light sheets are used, it is advantageous when they follow one another as seamlessly as possible in axial direction. Therefore, it is preferable that when at least one second light sheet is used, the light sheets are offset relative to one another in imaging direction by one half of the thickness of a light sheet.

BRIEF DESCRIPTION OF THE DRAWINGS

To avoid repetition in the description, elements which correspond to each other functionally or structurally in the different figures are always provided with the same reference numerals.

DETAILED DESCRIPTION OF EMBODIMENTS

It is to be understood that the figures and descriptions of the present invention have been simplified to illustrate elements that are relevant for a clear understanding of the present invention, while eliminating, for purposes of clarity, many other elements which are conventional in this art. Those of ordinary skill in the art will recognize that other elements are desirable for implementing the present invention. However, because such elements are well known in the art, and because they do not facilitate a better understanding of the present invention, a discussion of such elements is not provided herein.

The present invention will now be described in detail on the basis of exemplary embodiments.

Figure 1:
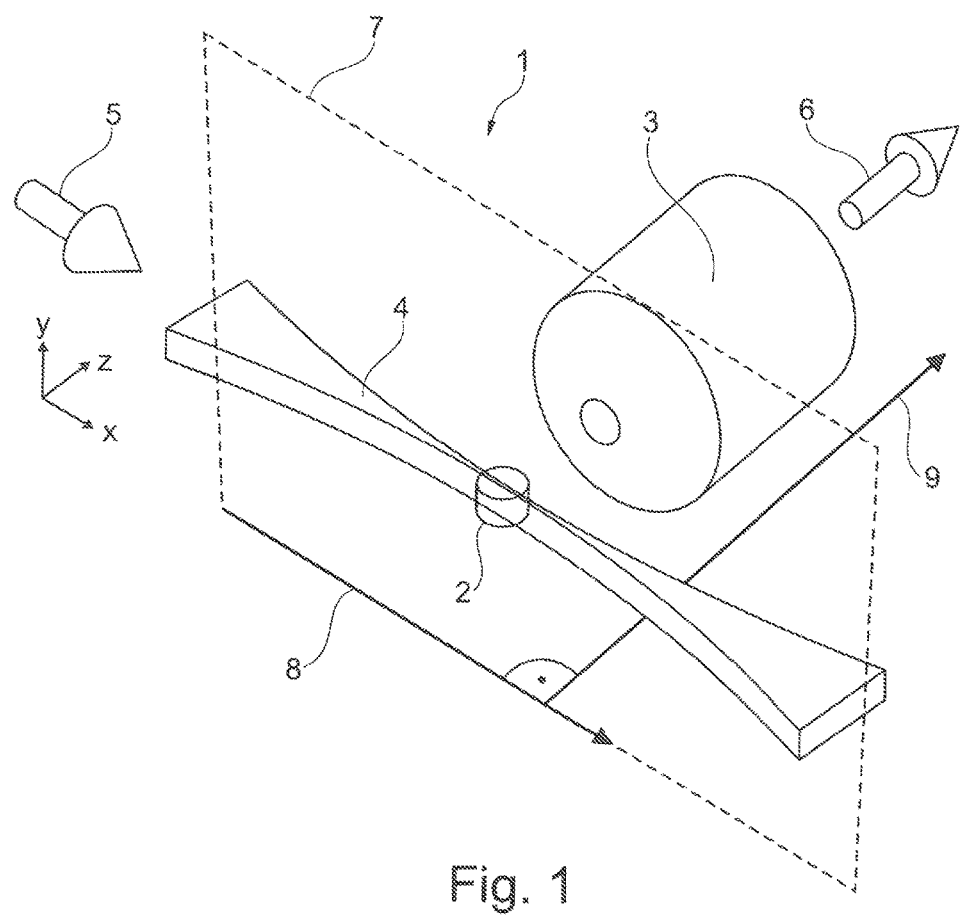
FIG. 1 shows a perspective schematic view of a microscope for 3D-high resolution localization fluorescence microscopy which is constructed as a further development of a light sheet microscope.

FIG. 1 schematically shows a microscope 1 which excites and images a sample 2 for fluorescence radiation. The microscope 1 is constructed for carrying out the PALM method. The sample 2 is imaged in wide field by an objective 3 on a detector (not shown further in FIG. 1). The excitation and/or activation of fluorescence radiation in the sample 2 is carried out with a light sheet 4 of activation radiation and/or excitation radiation coming from an excitation device 5. In the following description, it is assumed by way of example and without limiting generality that activation and excitation are carried out with radiation of the same wavelength as was described above in the introductory part of the specification with the example of molecules having a long-lived nonfluorescing state and a short-lived fluorescing state. For this reason, also, only excitation radiation is sometimes referred to in the following, although this may also mean switching radiation.

The sample 2 is imaged by the objective 3 on a detection device 6. The objective 3 establishes a plane of focus 7 which, as is well known, is surrounded by a depth of focus region which depends on the specific construction of the objective 3 and detection device 6.

It is an essential feature of the configuration of the microscope 1 as light sheet microscope that the excitation of the sample 2 through the light sheet 4 takes place along an excitation direction 8 extending substantially perpendicular to an imaging device 9 along which the sample 2 is imaged. This is characteristic of light sheet microscopy in which the illumination device is transverse to the imaging direction, generally perpendicular thereto.

Figure 2:
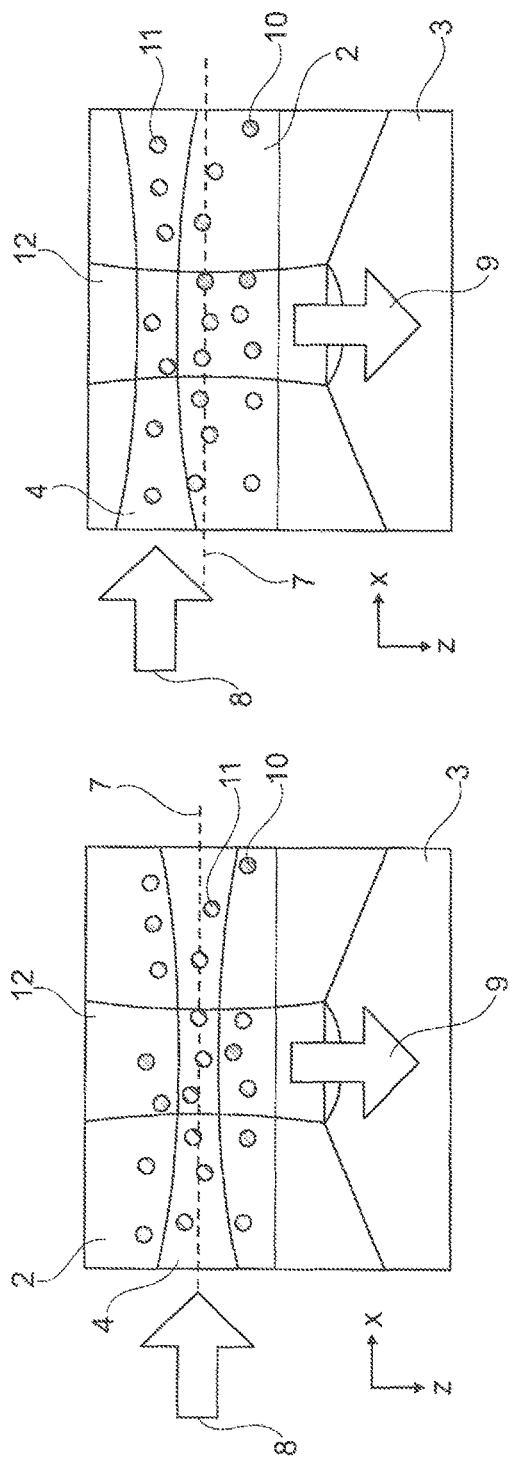
FIGS. 2 and 3 show schematic views for illustrating the position of the light sheet in the microscope from FIG. 1 relative to the plane of focus (top portions of FIGS. 2 and 3) and the point spread function generated in this way (bottom portion of Figures)
Figure 3:
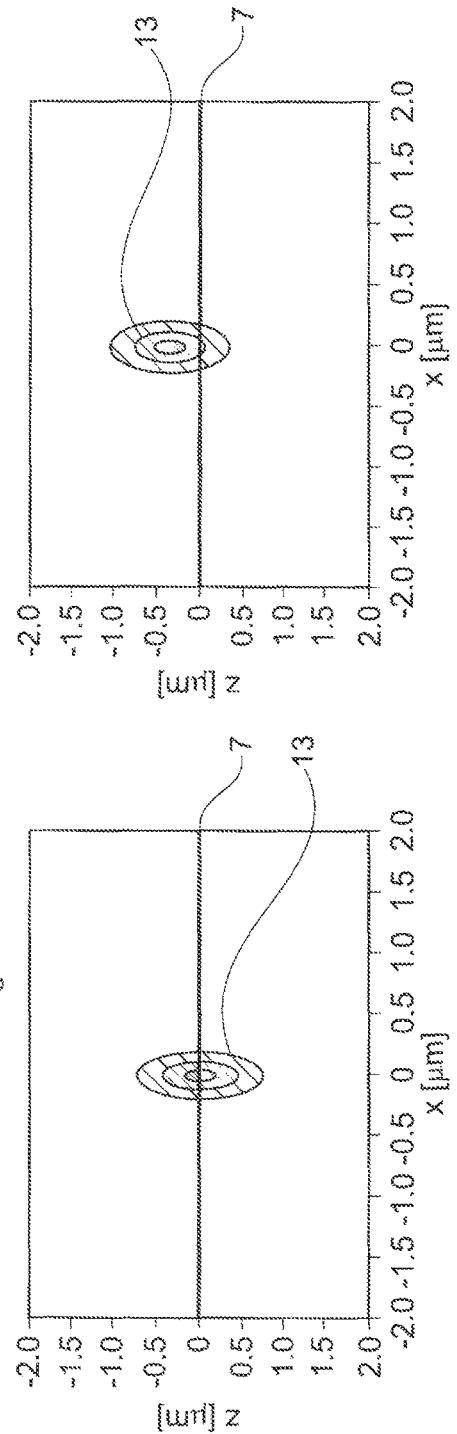

For the microscope in FIG. 1, the light sheet 4 is asymmetrical with respect to the plane of focus 7. The effect of this asymmetry is shown in FIGS. 2 and 3. Each of these figures contains two portions. The incidence of the light sheet 4 on the sample 2 and the imaging of luminescing fluorescence markers in the sample 2 are shown in a schematic sectional view in a top portion. The bottom portion of the figures shows a section through the point spread function in the x/z plane which is also selected as section plane in the top portion of the respective figure.

FIG. 2 shows the situation in the prior art when the light sheet is symmetric to the plane of focus 7. The view in FIGS. 2 and 3 shows non-luminescing fluorescence markers 10 and luminescing fluorescence markers 11. Owing to the PALM principle, they are only present, of course, in the volume of the sample 2 through which the light sheet passes. The fluorescence markers 10 are not excited in the volume of the sample 2 outside of the light sheet 4.

The bottom portion of FIG. 2 shows the PSF which is obtained in this setup. It is symmetric to the plane of focus 7 with respect to both its contour shape 13 and its intensity distribution.

These conditions change when the light sheet 4 is radiated symmetric to the plane of focus 7 as is shown in FIG. 3. In this case, the light sheet 4 is above the plane of focus 7. It is symmetrical with respect to its center plane only by way of example and not compulsorily. It is crucial that it is asymmetrical with respect to the plane of focus 7. As a result of this asymmetry of the light sheet 4 with respect to the plane of focus 7, the PSF is also asymmetrical, which is shown by the asymmetrical contour shape 13 of the bottom portion of FIG. 3. The PSF is shifted with respect to both contour shape 13 and intensity distribution relative to the plane of focus 7.

In the microscopy method carried out with the microscope in FIG. 1, this asymmetrical PSF is utilized for depth resolution in the PALM principle, i.e., for three-dimensional localization microscopy.

Figure 4:
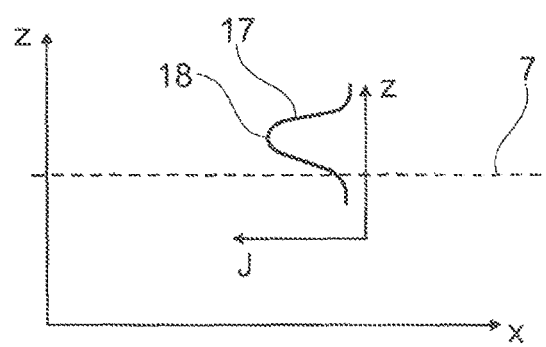
FIG. 4 shows a view similar to the top portion of FIG. 3, wherein, however, an intensity distribution of the light sheet is shown schematically.

FIG. 4 schematically shows a sectional view similar to the top and bottom portions of FIG. 3, i.e., a section in the x/z plane. The intensity distribution for the light sheet is shown here. It will be seen that the light sheet 4 has an intensity distribution 17 which is asymmetric to the plane of focus 7. While it is symmetrical per se, a maximum 18 of the intensity distribution 17 lies outside of the plane of focus 7. This causes the asymmetrical PSF shown in the bottom portion of FIG. 3. An asymmetrical PSF of this kind can also be obtained in an embodiment form in which the intensity distribution 17 is itself asymmetrical.

Figure 5A:
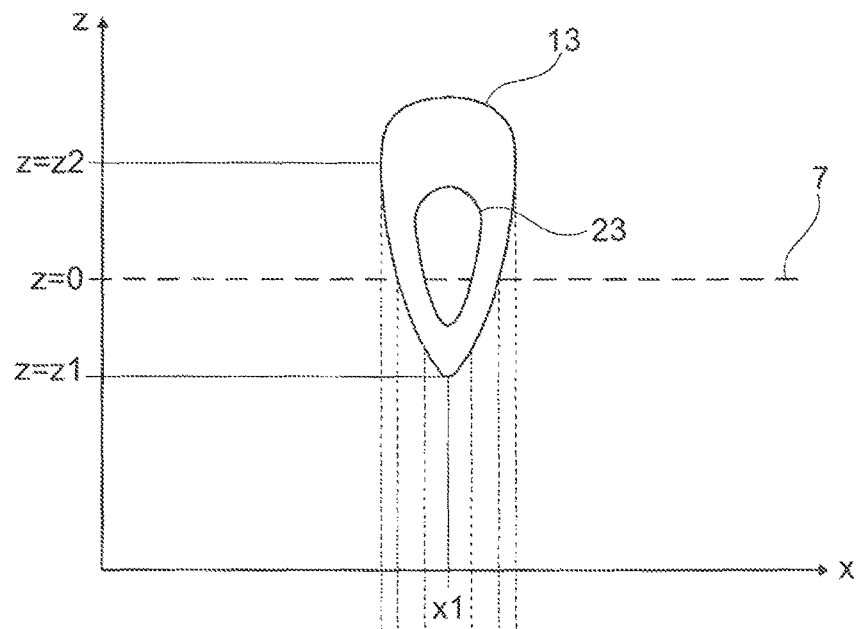
FIGS. 5a and b show the effect of an asymmetric point spread function according to the bottom portion of FIG. 3 (corresponding to FIG. 5a) on the size of diffraction disks in localization microscopy (FIG. 5b)
Figure 5B:
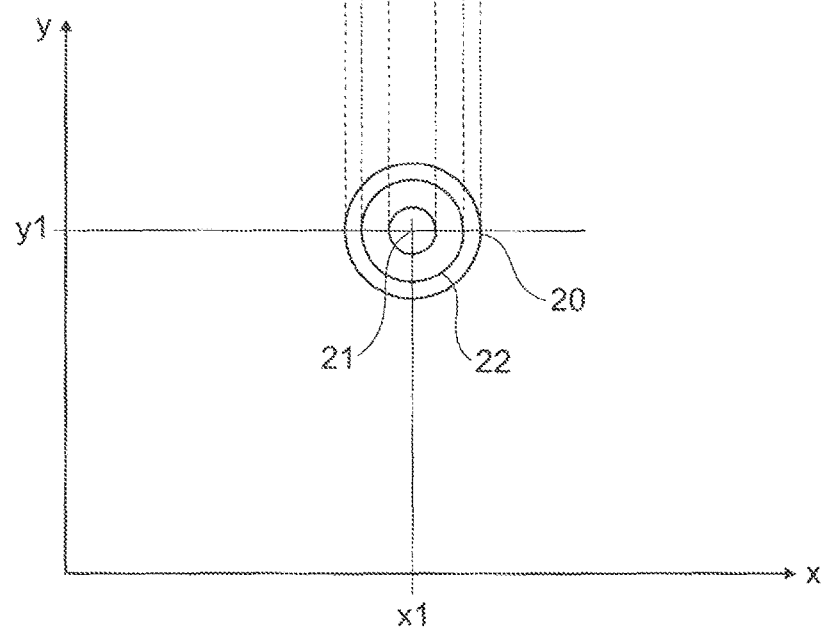

In three-dimensional localization microscopy, the sample is imaged in a plurality of image frames, and the parameters for generating these image frames are configured in a known manner such that at least some of the luminescing fluorescence markers 11 in the image frame are isolated with respect to the optical resolution given by the objective 3 and the detection device 6. The contour shape of each isolated fluorescence marker depends on the depth position of the luminescing fluorescence marker 11 owing to the asymmetry of the PSF. This is illustrated by FIGS. 5a and 5b. FIG. 5a shows the asymmetrical PSF in the x/z plane. It is asymmetrical with respect to the plane of focus 7. The luminescing fluorescence markers are imaged in a plane perpendicular to the y/z plane, which is an x/y plane in conventional Cartesian terminology and corresponding to the plot inserted in FIG. 1.

The contour shape of an imaged fluorescence marker depends on the z coordinate because the imaging is ultimately a section through the PSF of FIG. 5a. The result of this section is shown in FIG. 5b for three different z coordinates. As the z coordinate increases, there is an increase in the diameter of the contour shape which is shown in FIG. 5b as circular by way of example. Depending on the depth position, the diffraction disk 20 has a different diameter 22. The center 21 of the diffraction disk supplies the x coordinate and y coordinate of the location of the luminescing fluorescence marker. The z coordinate is derived from the diameter 22 of the contour shape. For this purpose, as was already described in the generic part of the specification, the actual contour shape 13 of the PSF is determined by simulation and/or measurement with respect to its localization and measurement of known point emitters.

The graph in FIG. 5a shows that, depending on asymmetry of the PSF, there may be cases in which the diameter 22, i.e., the contour shape of the diffraction disk 20, still does not allow an unequivocal depth correlation. For example, a location above position z2 could possibly give a diameter 22 for the diffraction disk 20 that corresponds approximately to the diameter for depth position z1. Therefore, it is provided in a preferred embodiment form that the brightness distribution of the diffraction disk 20 is also evaluated in addition to the contour shape, for example, of diameter 22. FIG. 5a shows that an unequivocal assignment of the depth position can be carried out in this way generally from analysis of the diffraction disk 20 because the intensity distribution 23 of the PSF is also asymmetrical.

This asymmetrical intensity distribution inside the contour shape 13 of the PSF is preferably also taken into account in determining the center 21.

Figure 6:
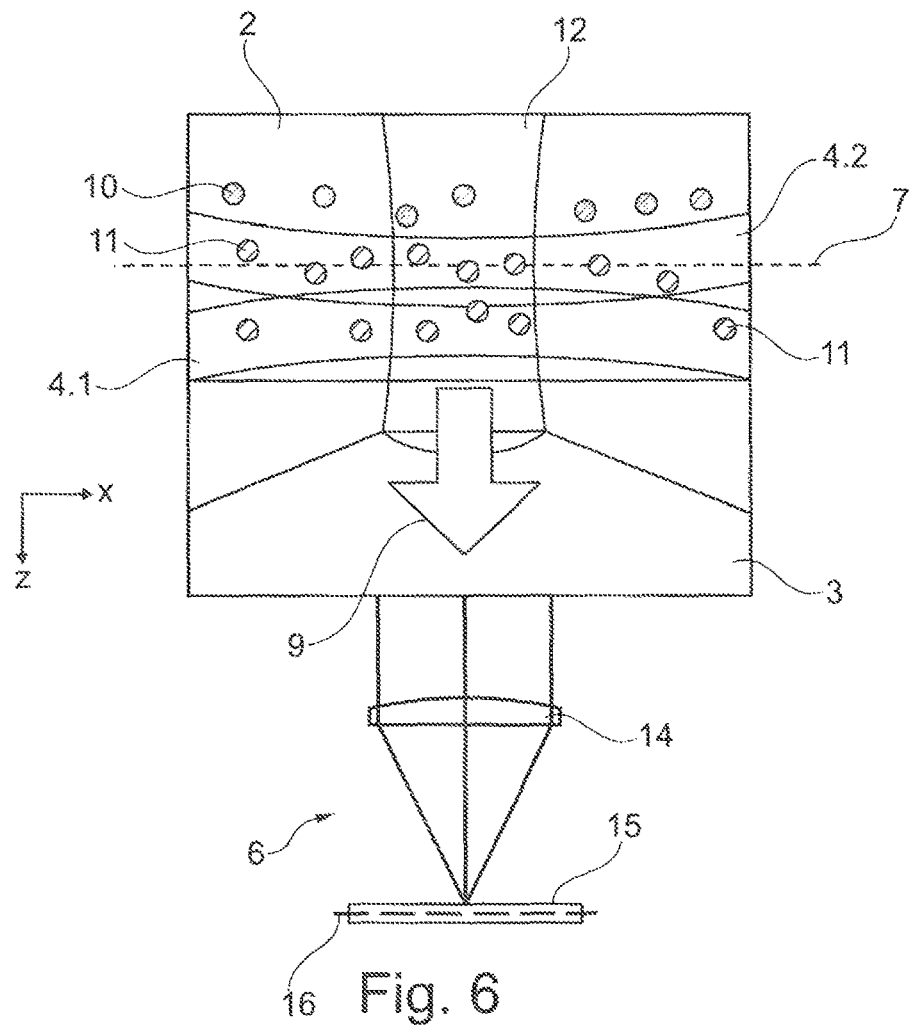
FIG. 6 shows a modified construction of the localization microscope of FIG. 1 in a schematic sectional view in which two light sheets are used.

FIG. 6 shows a further development of the microscope of FIG. 1 and the situation respecting illumination and detection in FIGS. 3/4 in which a second light sheet 4.2 extending relative to the plane of focus 7 by way of example in the embodiment form of FIG. 6 is emitted in addition to the asymmetric first light sheet designated by reference numeral 4.1 in FIG. 6. The sample 2 illuminated in this way is imaged in the detection device 6 via a tube lens 4 on a detector 15 which is arranged in a plane 16 conjugate to the plane of focus 7.

Thus, in addition to the first light sheet 4.1 which is asymmetrical with respect to the plane of focus 7, another, second light sheet 4.2 is radiated. The end result is an intensity distribution as shown schematically in FIG. 7. The two light sheets have intensity distributions 17.1 and 17.2 with a maximum 18.1 and 18.2, respectively. Intensity distribution 17.2 of the second light sheet is shown in dashes to distinguish it from intensity distribution 17.1. The total intensity distribution of the two light sheets 4.1 and 4.2 together is again asymmetric to the plane of focus 7. Accordingly, there likewise results an asymmetrical PSF which achieves an unambiguous axial localization and, therefore, three-dimensional localization microscopy. However, the acquired depth range is larger. In a preferred imaging, the light sheets abut each other seamlessly. This is achieved in that both light sheets are axially offset relative to a plane which does not coincide with the plane of focus 7, this offset corresponding in each instance to one half of the thickness of the corresponding light sheet.

The asymmetry of the PSF realized in FIG. 6 can also be achieved in an alternative embodiment by radiating only one light sheet which is asymmetrical with respect to the plane of focus 7 and by simultaneously observing with two opposing objectives 3 and detection devices 6. One of the two detection objectives 3 is focused on the plane of the light sheet, while the other is axially offset relative to the latter. This construction which is more technically complex has the added advantage that the photon yield is increased because photons which could normally not be detected by the detection device 6 because they are emitted in the opposite direction are now collected by the other detection objective.

Figure 8:
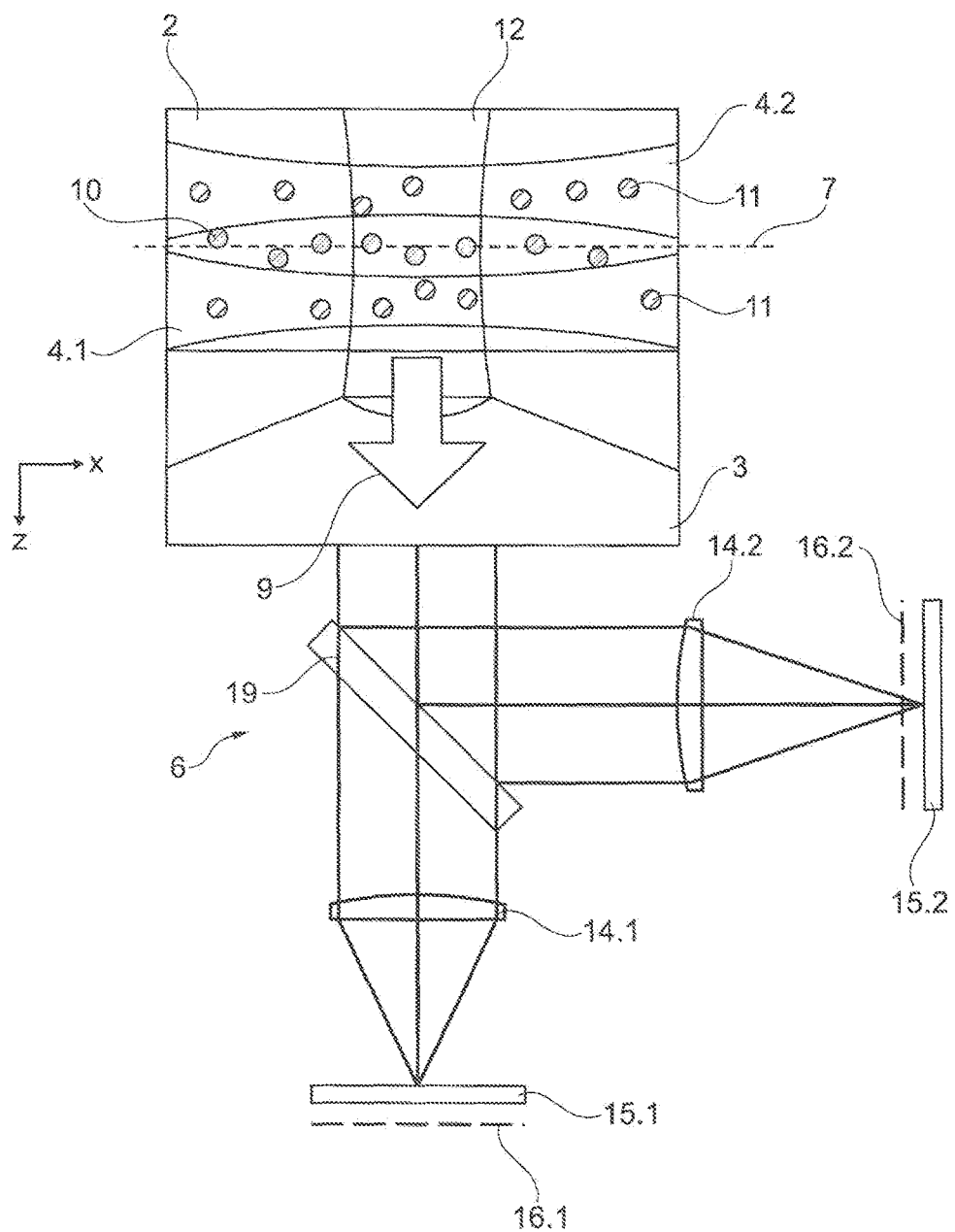
FIG. 8 shows a view similar to FIG. 6 for a further modification of a localization microscope with two light sheets.

FIG. 8 shows an alternative embodiment of the microscope 1 which again works with two light sheets 4.1 and 4.2 which, however, are now symmetric to one another. The first light sheet 4.1 and the second light sheet 4.2 are both asymmetric to the plane of focus 7. For this construction it is necessary to provide two detectors 15.1 and 15.2 which are offset in opposite directions relative to planes 16.1 and 16.2, respectively, which are conjugate to the plane of focus 7. One option for providing detectors of this type consists in splitting the beam path of objective 3, preferably formed as infinite beam path, by means of a 1:1 beamsplitter 19 and using two tube lenses 14.1, 14.2 which bundle the radiation into the conjugate plane 16.1 and 16.2, respectively.

The offset of the detectors 15.1 and 15.2 relative to the conjugate planes 16.1 and 16.2 exactly corresponds to the offset of the center of the light sheets 4.1 and 4.2, respectively, relative to the plane of focus 7. Each of the light sheets 4.1 and 4.2 asymmetric to the plane of focus 7 of the objective 3 generates an asymmetrical PSF. An unequivocal axial localization is possible by means of the corresponding orientation of the detectors 15.1 and 15.2 to the conjugate plane 16.1 and 16.2, respectively. The axially acquired area is accordingly increased as in the construction shown in FIG. 6.

Figure 7:
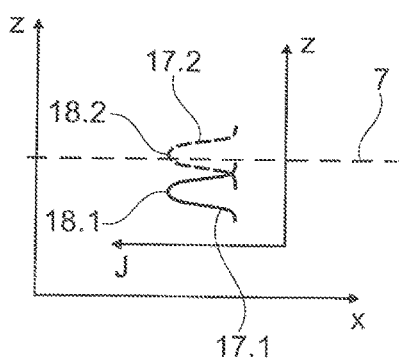
FIG. 7 shows a view similar to FIG. 4, but for the microscope of FIG. 6.
Figure 9:
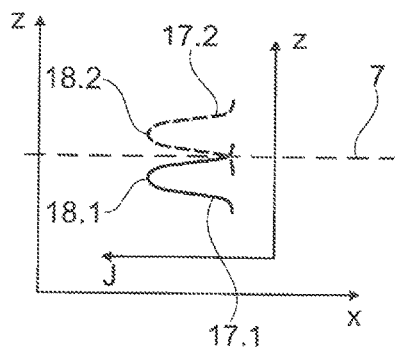
FIG. 9 shows a view corresponding to FIG. 7, but for the microscope of FIG. 8.

The intensity distribution of the light sheets 4.1 and 4.2 is shown in FIG. 9. It will be seen that the intensity distribution 17.1 is asymmetrical for the first light sheet 4.1 as well as for the second light sheet 4.2 whose intensity distribution 17.2 is shown in dashes in FIG. 9. The maxima 18.1 and 18.2 lie outside of the plane of focus 7 in each instance. As in the construction shown in FIG. 6, whose intensity distribution is shown in FIG. 7, the axially resolvable area is increased.

The construction in FIG. 8 has the drawback that the radiation collected by the objective 3 is split into two parts by the beamsplitter 19 so that only one half of the photon number can be used per detector 15.1, 15.2 for imaging. This results in a degraded signal-to-noise ratio. Accordingly, the localization accuracy is reduced. This disadvantage can be offset in a further development having two opposing detection objectives 3. In this case, no beamsplitter is needed, but rather two complete detection beam paths.

The plurality of light sheets according to the principle illustrated in FIG. 6 or 8 can, of course, also be expanded to three, four or more light sheets. This possibly increases the quantity of detectors required when the construction from FIG. 8 is used. Further, a beamsplitter and a tube lens are added with each additional detector.

When further light sheets are used, i.e., a plurality of light sheets in addition to the first light sheet 4.1, the further light sheets of course need not have the same thickness, especially not the same thickness as the first light sheet.

Figure 10:
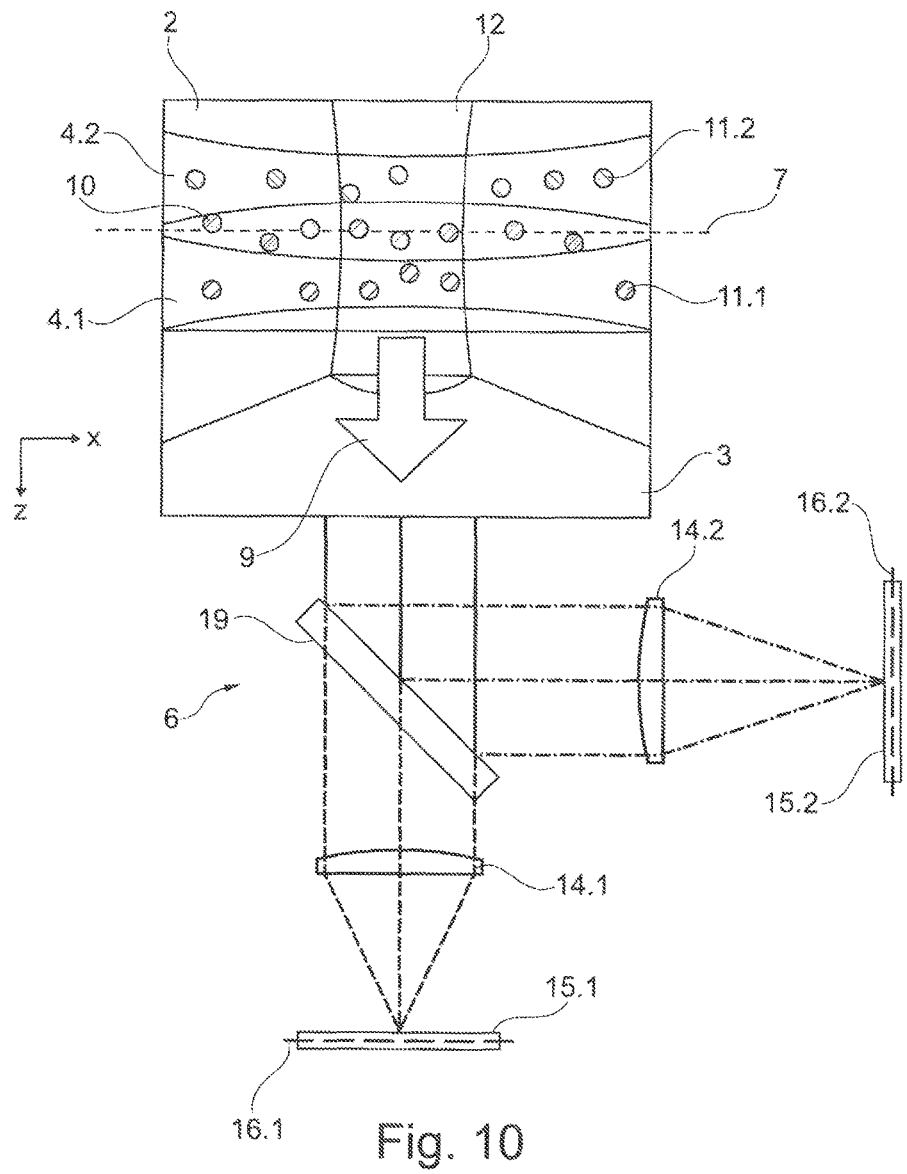
FIG. 10 shows a view similar to FIG. 6 for a further embodiment form of a light sheet microscope which likewise works with two different light sheets.

Aside from the biometric possibilities described above for generating an asymmetrical PSF by suitable light sheet illumination, it is possible in a further embodiment form to use the detection/excitation wavelength additionally in a suitable manner for interruption of symmetry. As is shown in FIG. 10, the sample can be illuminated by two light sheets 4.1 and 4.2 which are arranged asymmetrically with respect to the plane of focus 7. The sample 2 is again illuminated by two asymmetrical light sheets 4.1 and 4.2 which, in this case, differ in wavelength and therefore excite spectrally different fluorescences in the sample 2. This assumes that the sample 2 is labeled with two different species of fluorescence markers which differ with respect to their fluorescence characteristic. Alternatively, one and the same fluorescence marker can be used when it also emits spectrally different fluorescence radiation when excited in a spectrally different manner. These different fluorescence markers and differently excited fluorescence markers are distinguished in FIG. 10 by suffixes 0.1 and 0.2, respectively, corresponding to the reference numeral system used herein. Luminescing fluorescence markers 11.1 are formed under illumination by light sheet 4.1, luminescing fluorescence markers 11.2 are formed under illumination by light sheet 4.2. After imaging through objective 3, the radiation is split through a beamsplitter 19 which in this case is formed dichroically corresponding to the spectrum of the luminescing fluorescence markers 11.1 and 11.2.

The two light sheets 4.1 and 4.2 generate an asymmetrical PSF in each instance. Correlation is carried out through the wavelength so that the depth range is again doubled in total compared to the use of one light sheet.

In the embodiment forms described herein, it is assumed that the intensity distribution of the light sheets is such that the light sheets are radiated substantially parallel to the plane of focus 7. Of course, this is not absolutely necessary. In this respect, it is advisable to reference the plane of the maximum 18 of the intensity distribution 17 of the respective light sheet. However, this plane in which the maximum 18 lies need not necessarily be parallel to the plane of focus 7; it can also intersect the plane of focus 7 provided the intersection point is located outside the image area captured by the objective 3. In a construction such as this, the asymmetry of the PSF then depends on the x coordinate and/or y coordinate in the respective image frame. Of course, this must be taken into account in determining the depth information.

In some embodiment forms of the invention described herein, a plurality of light sheets are generated. There are a number of possibilities in this case.

When illuminating from two sides, i.e., one light sheet from a first side and one light sheet from a second side, the axial offset of the light sheets can easily be adjusted by different mirror positions.

Another variant uses a beamsplitter in the excitation device 5. A portion of the beam is coupled out of the beam path via a 1:1 beamsplitter and is then coupled into the beam path again at a different angle or with a small beam offset. The manipulation of this beam portion which is coupled out and then coupled in again allows two light sheets to be generated.

The typical exposure period of a detector in PALM microscopy is between 10 and 200 ms. A quasi-simultaneous illumination with a plurality of light sheets can be realized by fast multiplexing, for example, with a time period of less than 1 ms. Therefore, in the present description the concept of simultaneous illumination relates to the detection period in the imaging step. A suitably fast switching for quasi-simultaneous illumination can be achieved by means of galvanometer scanners, resonance scanners, MEMS scanners or acousto-optical deflectors (AODs). This quasi-simultaneous illumination has the advantage that the intensity of the two light sheets is automatically equally bright or can be adjusted over the time period of the respective illumination setting.

By means of an acousto-optical tunable filter (AOTF) and a scanner, a structured illumination can be realized in axial direction, i.e., more than one light sheet. The light sheet is continuously scanned in axial direction and the intensity is modulated simultaneously, e.g., sinusoidally, by means of the filter. In this way, a stripe illumination is generated in axial direction. The spacing of the stripes and, therefore, of the light sheets, is controlled by means of the modulation frequency. All of the light sheets are equally bright, and the spacing of the light sheets, i.e., the spacing between stripes, can be adjusted in a very precise manner. Any number of light sheets which preferably lie equidistant to one another can be generated in this way.

In a further variant, linearly polarized light is split uniformly by means of a birefringent crystal. The splitting can be controlled favorably via the angle of incidence. In this way, two light sheets can be generated by one crystal. Any even number of light sheets can be provided by using a plurality of birefringent crystals.

A further variant uses a segmented mirror. The respective mirror segments are not arranged in a parallel manner, but rather at a small angle relative to one another. Suitable imaging optics generate two spatially separated beams. The angle of the mirror segments together with the imaging optics determines the magnitude of the spatial separation of the light sheets in axial direction. In this way, any small distances between the light sheets can also be provided in a stable manner. Motor-actuated mirror elements which allow a change in angle of the individual mirror segments and, therefore, an adjustment of the axial offset of the light sheets, are known in the art, for example, from astronomy and adaptive optics.

By means of suitable polarization-dependent beamsplitters, mean light sheets can be generated in conjunction with a half-wave plate. The exit angle of the light sheets depends on the type of beamsplitter.

In a further variant with a spatial light modulator in the illumination beam path, the phase and amplitude of the beam path is manipulated. By adjusting a complex amplitude distribution, a plurality of light sheets are generated. A scanning of the light sheets in all spatial directions is likewise provided in a further development.

In a further variant, two divided phase plates having a relative phase offset of 90° generate a double-lightsheet.

While this invention has been described in conjunction with the specific embodiments outlined above, it is evident that many alternatives, modifications, and variations will be apparent to those skilled in the art. Accordingly, the preferred embodiments of the invention as set forth above are intended to be illustrative, not limiting. Various changes may be made without departing from the spirit and scope of the inventions as defined in the following claims.

The invention claimed is:

1. A method for three-dimensional high-resolution localization microscopy comprising:
    illuminating a sample by excitation radiation in an excitation step so as to excite fluorescence markers in the sample to luminesce;
    imaging the sample in an image frame in an imaging step by means of imaging optics along an imaging direction, wherein the image frame contains images of the luminescing fluorescence markers, and the imaging optics have a plane of focus and an optical resolution;
    repeating the excitation step and imaging step multiple times to generate a plurality of image frames;
    isolating images of the luminescing fluorescence markers in each image frame for at least some of the luminescing fluorescence markers;
    determining a location of the corresponding fluorescence marker in each instance in the generated plurality of image frames from the isolated images of the luminescing fluorescence markers, which location has an accuracy exceeding the optical resolution; and
    generating a highly resolved total from the determined locations;
    wherein the excitation radiation is passed into the sample as a first light sheet having along the imaging direction an intensity distribution that is asymmetric to the plane of focus; and
    wherein the isolated images of the luminescing fluorescence markers are each analyzed with respect to a contour shape thereof in the image frames, and a z coordinate indicating a distance of the corresponding fluorescence marker from the plane of focus is derived from a diameter of the contour shape.

2. The method according to claim 1;
    wherein the sample is imaged on a detector lying in a plane conjugate to the plane of focus in the imaging step.

3. The method according to claim 1;
    wherein the intensity distribution has a maximum which lies outside the plane of focus.

4. The method according to claim 1;
    wherein a second light sheet which does not overlap with the first light sheet is radiated in the sample.

5. The method according to claim 4;
    wherein the second light sheet is symmetric to the first light sheet with respect to the plane of focus; and
    wherein the sample is imaged on two detectors in the imaging step, one of the two detectors being located in front of a plane which is conjugate to the plane of focus and the other of the two detectors being located behind a plane which is conjugate to the plane of focus.

6. The method according to claim 4;
    wherein a wavelength spectrum of the first light sheet is different from a wavelength spectrum of the second light sheet.

7. The method according to claim 1;
    wherein a second light sheet having an intensity distribution symmetric to the plane of focus is radiated in the sample.

8. A method for three-dimensional high-resolution localization microscopy comprising:
    illuminating a sample by excitation radiation in an excitation step so as to excite fluorescence markers in the sample to luminesce;
    imaging the sample in an image frame in an imaging step by means of imaging optics along an imaging direction, wherein the image frame contains images of the luminescing fluorescence markers, and the imaging optics have a plane of focus and an optical resolution;
    repeating the excitation step and imaging step multiple times to generate a plurality of image frames;
    isolating images of the luminescing fluorescence markers in each image frame for at least some of the luminescing fluorescence markers;
    determining a location of the corresponding fluorescence marker in each instance in the generated plurality of image frames from the isolated images of the luminescing fluorescence markers, which location has an accuracy exceeding the optical resolution; and
    generating a highly resolved total from the determined locations;
    wherein the excitation radiation is passed into the sample as a first light sheet having along the imaging direction an intensity distribution that is asymmetric to the plane of focus; and
    wherein the isolated images of the luminescing fluorescence markers are each analyzed with respect to a contour shape thereof in the image frames, and information about a distance of the corresponding fluorescence marker from the plane of focus is derived from the contour shape;
    wherein a second light sheet is radiated in the sample; and
    wherein the first and second light sheets are offset relative to one another by one half of the light sheet thickness in the imaging direction.

* * * * *